(12) United States Patent
Sekiguchi (10) Patent No.: US 7,887,480 B2
(45) Date of Patent: Feb. 15, 2011

(54) BALLOON CONTROL APPARATUS (75) Inventor: Tadashi Sekiguchi, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 972 days.

(21) Appl. No.: 11/703,693

(22) Filed: Feb. 8, 2007

(65) Prior Publication Data
US 2007/0191678 A1 Aug. 16, 2007

(30) Foreign Application Priority Data
Feb. 10, 2006 (JP) ............................ P2006-034394

(51) Int. Cl.
A61B 1/04 (2006.01)
A61M 29/00 (2006.01)
(52) U.S. Cl. ................. 600/116; 600/114; 600/115; 604/97.01; 604/99.01
(58) Field of Classification Search ......... 600/114–116, 600/118; 604/96.01–103.14
See application file for complete search history.

(56) References Cited

U.S. PATENT DOCUMENTS

| 6,328,690 | B1 | 12/2001 | Takami et al. | |
|---|---|---|---|---|
| 2004/0215060 | A1* | 10/2004 | Ueno et al. | 600/160 |
| 2005/0197861 | A1* | 9/2005 | Omori et al. | 705/2 |
| 2005/0222496 | A1* | 10/2005 | Sekiguchi | 600/115 |
| 2007/0038026 | A1 | 2/2007 | Yoshida et al. | |
| 2009/0306633 | A1* | 12/2009 | Trovato et al. | 604/891.1 |

FOREIGN PATENT DOCUMENTS

| EP | 1654975 A1 | 5/2006 |
|---|---|---|
| EP | 1731084 A1 | 12/2006 |
| JP | 2002-301019 A | 10/2002 |
| JP | 2004-337288 A | 12/2004 |
| JP | 2005-261782 A | 9/2005 |
| WO | WO-2005/089625 A1 | 9/2005 |

* cited by examiner

Primary Examiner—Thomas J Sweet
Assistant Examiner—Ryan Henderson
(74) Attorney, Agent, or Firm—Birch, Stewart, Kolasch & Birch, LLP (57) ABSTRACT A balloon control apparatus includes a balloon, a flow rate adjustment section, a setting section and a control section. The balloon is attached to an insertion section of an endoscope and/or an insertion aid instrument for guiding insertion of the insertion section of the endoscope. The flow rate adjustment section adjusts an air supply flow rate to the balloon and/or an exhaust flow rate from the balloon. The setting section sets the air supply flow rate and/or the exhaust flow rate. The control section controls the flow rate adjustment section so that the air supply flow rate to the balloon and/or the exhaust flow rate from the balloon become the air supply flow rate and/or the exhaust flow rate set by the setting section.

8 Claims, 9 Drawing Sheets

BALLOON CONTROL APPARATUS

BACKGROUND OF THE INVENTION

1. Technical Field

This invention relates to a balloon control apparatus and in particular to a balloon control apparatus that can eliminate (or lessen) difference in time until the balloon internal pressure reaches a predetermined pressure (namely, the time until the balloon is fixed) regardless of the type of digestive tract.

2. Description of the Related Art

Hitherto, in the field of an endoscope, the following endoscope with a balloon has been known. That is, from the viewpoint of fixing to a body cavity an endoscope insertion section (or an insertion aid instrument for guiding insertion of the endoscope insertion section) inserted into the body cavity, the endoscope has the balloon, which is expanded by air supply and contracted by exhaust, in the endoscope insertion section (or the insertion aid instrument; see JP 2002-301019 A and JP 2004-337288 A).

In the endoscope with the balloon, an air pump is connected to the balloon via a tube, etc.

As an air supply (pressurizing) switch is turned on, the air pump starts air supply, whereby the balloon starts to expand. After a while, the balloon expands and contacts an intestinal wall, etc., and the balloon internal pressure reaches a predetermined setup pressure.

Thus, when the balloon internal pressure reaches the predetermined setup pressure (for example, 5.6 kPa), the air pump is controlled so as to stop air supply.

On the other hand, as an exhaust (decompression) switch is turned on, the air pump starts exhaust, whereby the balloon starts to contract. After a while, the balloon contracts and the balloon internal pressure reaches a predetermined setup pressure.

Thus, when the balloon internal pressure reaches the predetermined setup pressure, the air pump is controlled so as to stop exhaust.

By the way, digestive tracts differ in diameter from one type to another (for example, a small intestine is about 25 mm in diameter and a large intestine is about 35 mm in diameter). Nevertheless, in the endoscope with the balloon according to the related art, air supply to the balloon or exhaust from the balloon is executed at a predetermined flow rate. Thus, the time required until the balloon expands and contacts an intestinal wall and the balloon internal pressure reaches a predetermined pressure varies from one digestive tract to another. For example, according to an experiment carried out by the inventor (assuming that the average diameter of a small intestine is about 25 mm and the average diameter of a large intestine is about 35 mm, air was supplied to a balloon placed in each intestine at a predetermined flow rate), the time required until the balloon expands and contacts the intestinal wall and the balloon internal pressure reaches a predetermined pressure was about 10 seconds for the small intestine and about 30 seconds for the large intestine.

Thus, in the endoscope with the balloon according to the related art, since air supply to the balloon (or exhaust from the balloon) is executed at a predetermined flow rate, the time until the balloon internal pressure reaches a predetermined pressure (namely, the time until the balloon is fixed) varies depending on the type of digestive tract, and the ease of operation is poor.

SUMMARY OF THE INVENTION

The invention provides a balloon control apparatus that can eliminate (or lessen) the difference in time until the balloon internal pressure reaches a predetermined pressure (namely, the time until the balloon is fixed) regardless of the type of digestive tract.

According to an aspect of the invention, a balloon control apparatus includes a balloon, a flow rate adjustment section, a setting section and a control section. The balloon is attached to an insertion section of an endoscope and/or an insertion aid instrument for guiding insertion of the insertion section of the endoscope. The flow rate adjustment section adjusts an air supply flow rate to the balloon and/or an exhaust flow rate from the balloon. The setting section sets the air supply flow rate and/or the exhaust flow rate. The control section controls the flow rate adjustment section so that the air supply flow rate to the balloon and/or the exhaust flow rate from the balloon become the air supply flow rate and/or the exhaust flow rate set by the setting section.

According to this configuration, the setting section can set any desired air supply flow rate (or exhaust flow rate). For example, the air supply flow rate (or exhaust flow rate) may be set in accordance with the intracoelomic part into which the endoscope insertion section, etc., is to be inserted (for example, digestive tract of small intestine, large intestine, etc.).

Also, the balloon control apparatus may further include a part selection section that allows an operator to select an intracoelomic part into which the insertion section of the endoscope and/or the insertion aid instrument is to be inserted. The setting section sets the air supply flow rate or the exhaust flow rate in accordance with the intracoelomic part selected by the part selection section.

According to this configuration, it is made possible to set the air supply flow rate (or exhaust flow rate) in accordance with the intracoelomic part into which the endoscope insertion section, etc., is to be inserted (for example, digestive tract of small intestine, large intestine, etc.,) through the setting section. That is, it is made possible to set the flow rate in response to the intracoelomic part (for example, the type of digestive tract) in such a manner that if a small intestine is selected, flow rate R is set or if a large intestine is selected, flow rate R1×3 is set. Formerly, the time required until the balloon expands and contacts the intestinal wall and predetermined pressure P is reached was about 10 seconds for the small intestine and about 30 seconds for the large intestine. To the contrary, according to this above configuration, the flow rates are set as described above. Thereby, the time until the internal pressure of the balloon reaches the setup pressure P (namely, the time until the balloon is fixed) in the large intestine becomes about one third and becomes roughly equal to the required time in the small intestine. That is, it is made possible to eliminate (or lessen) the difference in time until the internal pressure of the balloon reaches the setup pressure P (namely, the time until the balloon is fixed) regardless of the type of digestive tract. The ease of operation is improved and efficient inspection and medical treatment are made possible.

Also, the balloon control apparatus may further include a procedure selection section that allows an operator to select a procedure of the endoscope. The setting section sets the air supply flow rate or the exhaust flow rate in accordance with the procedure selected by the procedure selection section.

According to this configuration, it is made possible to set the air supply flow rate (or exhaust flow rate) in accordance with the procedure of the endoscope, such as a single balloon method or a double balloon method, through the setting section. That is, it is made possible to set the flow rate in accordance with the procedure in such a manner that if the operator selects the single balloon method, flow rate R1 is set and that if the operator selects the double balloon method, flow rate R2 (R1>R2) is set. Formerly, the single balloon method and the double balloon method were roughly the same in the time required until the balloon expands and contacts the intestinal wall and the predetermined pressure P is reached. To the contrary, according to the above configuration, the flow rates are set as described above. Thereby, the expansion and contraction time of the single balloon is shortened and return of the pulled-in intestinal tract can be lessened. As a result, the single balloon method would also make it possible to improve the ease of operation and conduct efficient inspection and medical treatment.

Also, the balloon control apparatus may further include an attribute specification section that allows an operator to specify an attribute of a subject into whom the insertion section of the endoscope and/or the insertion aid instrument is to be inserted. The setting section sets the air supply flow rate or the exhaust flow rate in accordance with to the intracoelomic part selected by the part selection section and the attribute of the subject specified by the attribute specification section.

According to this configuration, it is made possible to set the air supply flow rate or the exhaust flow rate in accordance with not only the intracoelomic part selected by the part selection section (for example, digestive tract of small intestine, large intestine, etc.), but also the attribute of the subject specified by the attribute specification section (gender, age, etc.).

Also, the intracoelomic part into which the insertion section of the endoscope and/or the insertion aid instrument is to be inserted may be a digestive tract.

According to this configuration, it is made possible to set the air supply flow rate or the exhaust flow rate in accordance with the type of digestive tract into which the endoscope insertion section, etc., is to be inserted According to another aspect of the invention, An endoscope system includes a balloon, a flow rate adjustment section, a setting section, a control section, a connection part and a use determination section. The balloon is attached to an insertion section of an endoscope and/or an insertion aid instrument for guiding insertion of the insertion section of the endoscope. The flow rate adjustment section adjusts an air supply flow rate to the balloon and/or an exhaust flow rate from the balloon. The setting section sets an air supply flow rate and/or an exhaust flow rate. The control section controls the flow rate adjustment section so that the air supply flow rate to the balloon and/or the exhaust flow rate from the balloon become the air supply flow rate and/or the exhaust flow rate set by the setting section. The endoscope is connected to the connection part. The use determination section determines a use of the endoscope connected to the connection part. The setting section sets the air supply flow rate or the exhaust flow rate in accordance with the use of the endoscope determined by the use determination section.

According to this configuration, when the endoscope is connected, it is made possible to automatically recognize the use of the endoscope (for example, large intestine endoscope or small intestine endoscope) and set the air supply flow rate and/or the exhaust flow rate in response to the endoscope.

Also, the use determination section may include a reading section that reads an identifier from the endoscope connected to the connection part and determines the use of the endoscope connected to the connection part based on the identifier read by the reading section.

According to this configuration, when the endoscope is connected, it is made possible to read the identifier (for example, endoscope ID) from the endoscope, automatically recognize the use of the endoscope (for example, large intestine endoscope or small intestine endoscope), and set the air supply flow rate and/or the exhaust flow rate in response to the endoscope.

According to the invention, it is made possible to provide the balloon control apparatus that can eliminate (or lessen) the difference in time until a balloon is fixed (namely, the time until the balloon internal pressure reaches the setup pressure P) regardless of the type of digestive tract; the ease of operation improves and efficient inspection and medical treatment are made possible.

DETAILED DESCRIPTION OF EMBODIMENTS OF THE INVENTION

Figure 1:
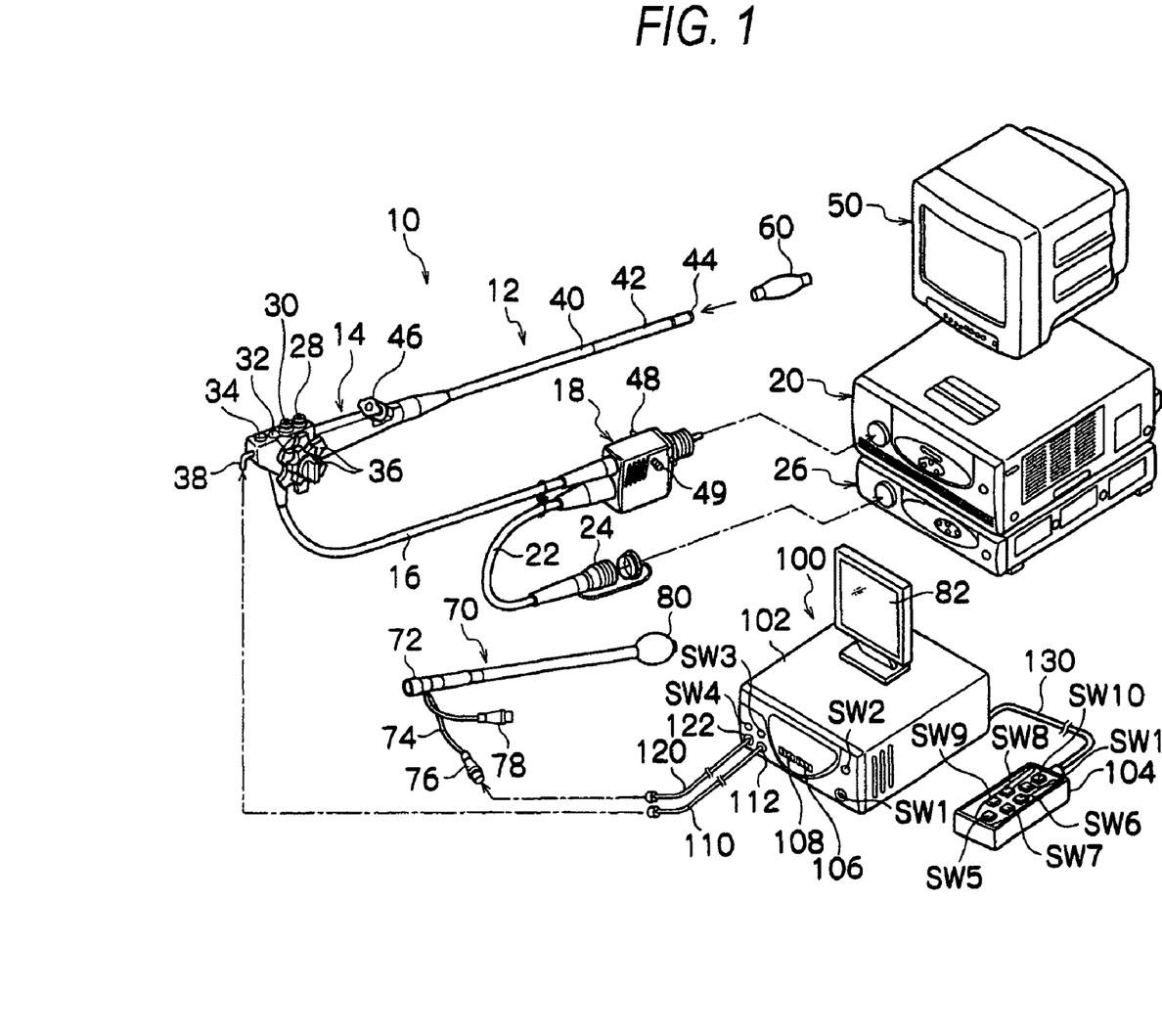
FIG. 1 is a system configuration drawing to show an endoscope system incorporating a balloon control apparatus according to one embodiment of the invention.

A balloon control apparatus for an endoscope according to exemplary embodiments of the invention will be described in detail with reference to the accompanying drawings. FIG. 1 is a system configuration drawing to show an endoscope system incorporating a balloon control apparatus according to one embodiment of the invention. As shown in FIG. 1, the endoscope system mainly includes an endoscope 10, an insertion aid instrument 70, and a balloon control apparatus 100.

As shown in FIG. 1, the endoscope 10 includes a handheld operation section 14 and an insertion section 12 which is jointed to the handheld operation section 14 and which is inserted into a body cavity. A universal cable 16 is connected to the handheld operation section 14. An LG connector 18 is provided at the tip of the universal cable 16. The LG connector 18 is detachably joined to a light source unit 20, to thereby send illumination to an illumination optical system 54 (described later with reference to FIG. 2). An electric connector 24 is connected to the LG connector 18 through a cable 22 and is detachably joined to a processor 26.

The handheld operation section 14 is provided with an air supply-water supply button 28, a suction button 30, a shutter button 32, and a function switch button 34 side by side and is also provided with a pair of angle knobs 36 and 36. A balloon air supply port 38 is formed of a tube bent like a letter L, at a base end of the handheld operation section 14. Fluid of air, etc., is supplied to or suctioned from the balloon air supply port 38, whereby a first balloon 60 described later can be expanded or contracted.

The insertion section 12 includes a soft part 40, a bend part 42, and a tip part 44 in order from the side of the handheld operation section 14. An operator remotely performs a bend operation of the bend part 42 by rotating the angle knob 36, 36 of the handheld operation section 14. Accordingly, the tip part 44 can be directed in any desired direction.

Figure 2:
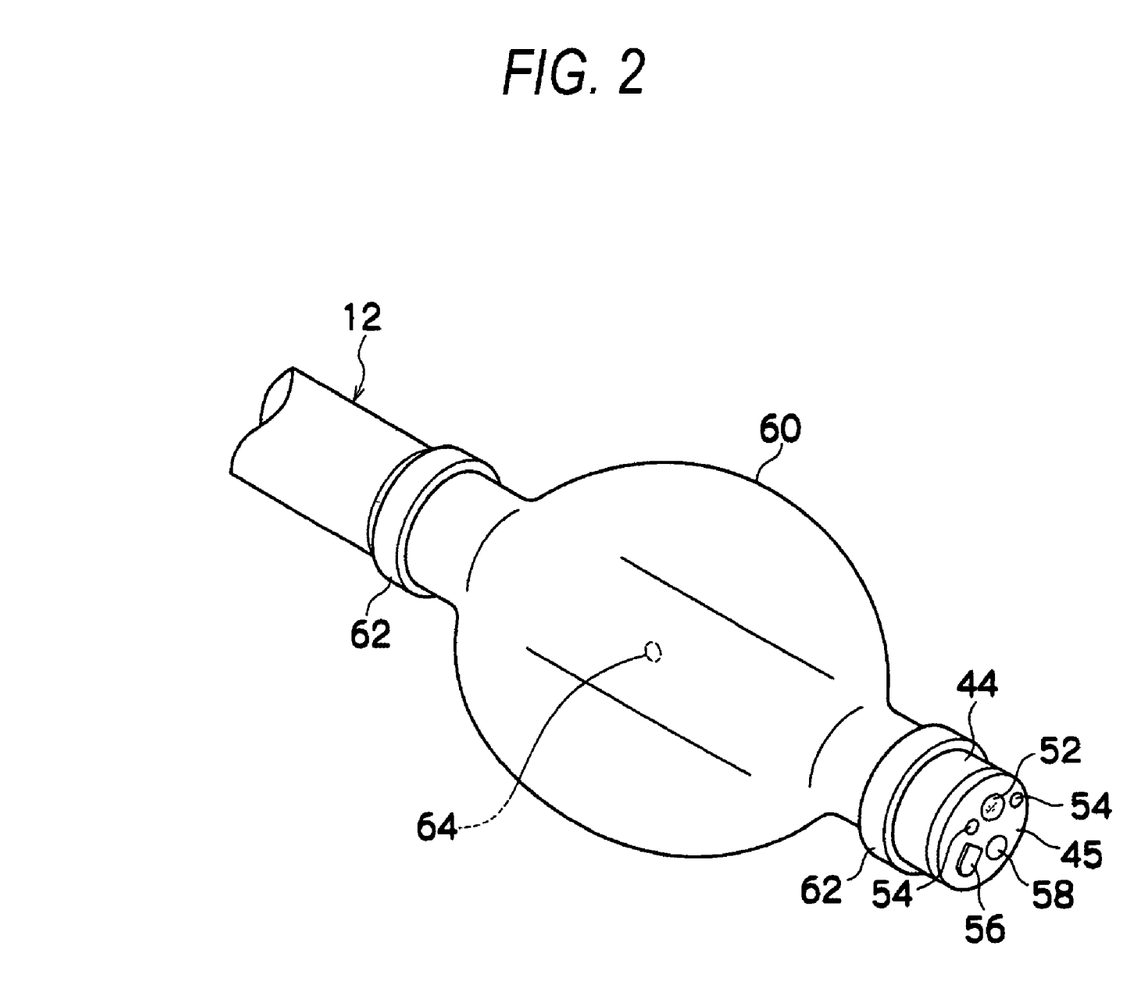
FIG. 2 is a perspective view of a tip part of an endoscope insertion section.

As shown in FIG. 2, an observation optical system 52, the illumination optical system 54, 54, an air supply-water supply nozzle 56, and a forceps slot 58 are provided on a tip face 45 of the tip part 44. CCD (not shown) is disposed behind the observation optical system 52 and a signal cable (not shown) is connected to a board for supporting the CCD. The signal cable is inserted into the insertion section 12, the handheld operation section 14, and the universal cable 16 in FIG. 1, is extended to the electric connector 24, and is connected to the processor 26. Therefore, an observation image input through the observation optical system 52 is formed on the light reception face of the CCD and is converted into an electric signal. This electric signal is output through the signal cable to the processor 26 and is converted into a video signal. Accordingly, the observation image is displayed on a monitor 50 connected to the processor 26.

An emission end of a light guide (not shown) is disposed behind the illumination optical system 54, 54 in FIG. 2. The light guide is inserted into the insertion section 12, the handheld operation section 14, and the universal cable 16 in FIG. 1 and has an incidence end disposed in the LG connector 18. Therefore, the LG connector 18 is joined to the light source unit 20, whereby illumination light emitted from the light source unit 20 is transmitted through the light guide to the illumination optical system 54, 54 and is applied forward from the illumination optical system 54, 54.

The air supply-water supply nozzle 56 in FIG. 2 is communicated with a valve (not shown) operated by operating the air supply-water supply button 28 in FIG. 1 and further the valve is communicated with an air supply-water supply connector 48 provided in the LG connector 18. Air supply-water supply means (not shown) is connected to the air supply-water supply connector 48 for supplying air or water. Therefore, the operator can jet air or water through the air supply-water supply nozzle 56 toward the observation optical system 52.

The forceps slot 58 in FIG. 2 is communicated with a forceps insertion part 46 in FIG. 1. Thus, a treatment tool of a forceps, etc., is inserted from the forceps insertion part 46, whereby the treatment tool can be derived from the forceps slot 58. The forceps slot 58 is communicated with a valve (not shown) operated by operating the suction button 30 and further the valve is communicated with a suction connector 49 of the LG connector 18. Therefore, suction means (not shown) is connected to the suction connector 49 and the valve is operated by operating the suction button 30, whereby a lesion part, etc., can be suctioned from the forceps slot 58.

The first balloon 60 made of an elastic body of rubber, etc., is attached to the outer peripheral surface of the insertion section 12. The first balloon 60 is formed roughly like a tube with both end parts narrowed. The insertion section 12 is inserted into the first balloon 60 and the first balloon 60 is placed at any desired position and then rubber fix rings 62 and 62 are fitted into both end parts of the first balloon 60 as shown in FIG. 2, whereby the first balloon 60 is fixed to the insertion section 12.

A vent hole 64 is made in the outer peripheral surface of the insertion section 12 as the attachment position of the first balloon 60. The vent hole 64 is communicated with the balloon air supply port 38 provided on the handheld operation section 14 in FIG. 1 and the balloon air supply port 38 is connected to the balloon control apparatus 100 through a tube 110 (described later). Therefore, the balloon control apparatus 100 supplies air and sucks air (also called exhausts), whereby the first balloon 60 can be expanded and contracted. Air is supplied to the first balloon 60, which then is expanded roughly like a sphere; air is suctioned from the first balloon 60, which then is put on the outer surface of the insertion section 12.

On the other hand, the insertion aid instrument 70 shown in FIG. 1 is formed like a pipe and has an inner diameter slightly larger than the outer diameter of the insertion section 12 and also includes sufficient flexibility. A hard grip part 72 is provided at the base end of the insertion aid instrument 70 and the insertion section 12 is inserted from the hard grip part 72.

A second balloon 80 is attached in the proximity of the tip of the insertion aid instrument 70. The second balloon 80 is formed roughly like a tube with both ends narrowed and is attached in a state in which the insertion aid instrument 70 pierces the second balloon 80, and a thread (not shown) is wound around the second balloon 80 to fix the second balloon 80. A tube 74 put on the outer peripheral surface of the insertion aid instrument 70 is communicated with the second balloon 80, and a connector 76 is provided at the base end of the tube 74. A tube 120 is connected to the connector 76 and the connector 76 is connected to the balloon control apparatus 100 through the tube 120. Therefore, the balloon control apparatus 100 supplies air and sucks air, whereby the second balloon 80 can be expanded and contracted. Air is supplied to the second balloon 80, which then is expanded roughly like a sphere; air is suctioned from the second balloon 80, which then is put on the outer surface of the insertion aid instrument 70.

An injection port 78 is provided on the base end side of the insertion aid instrument 70. The injection port 78 is communicated with an opening (not shown) formed on the inner peripheral surface of the insertion aid instrument 70. Therefore, a lubricant (for example, water, etc.,) is injected with an injector, etc., from the injection port 78, whereby it can be supplied to the inside of the insertion aid instrument 70. Thus, when the insertion section 12 is inserted into the insertion aid instrument 70, the friction between the inner peripheral surface of the insertion aid instrument 70 and the outer peripheral surface of the insertion section 12 can be decreased and a relative move between the insertion section 12 and the insertion aid instrument 70 can be made smoothly.

The balloon control apparatus 100 is an apparatus for supplying and sucking fluid of air, etc., to and from the first balloon 60 and supplying and sucking fluid of air, etc., to and from the second balloon 80. The balloon control apparatus 100 is mainly made up of an apparatus main unit 102 and a hand switch 104 for remote control.

Figure 3:
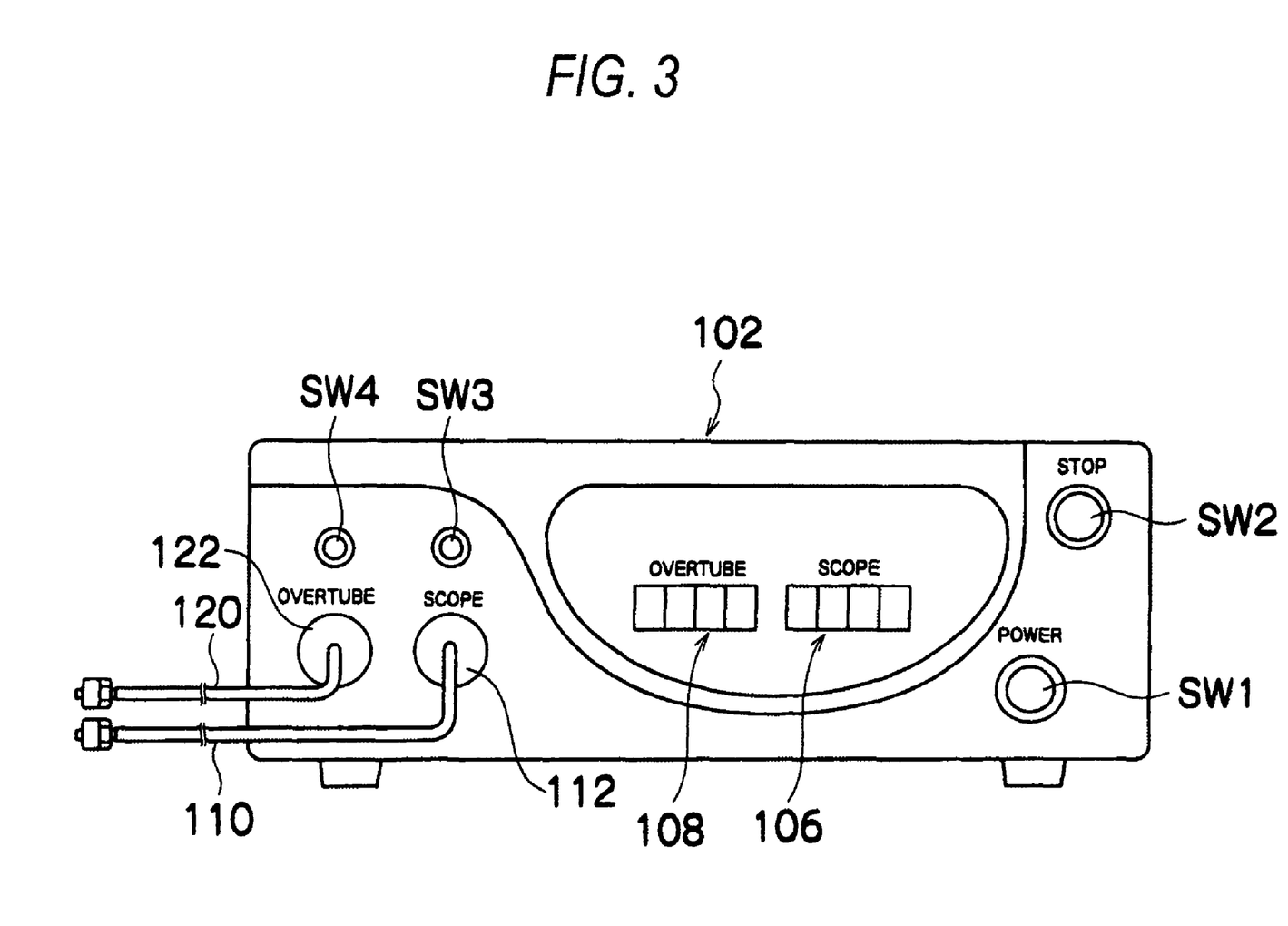
FIG. 3 is a front view of the balloon control apparatus.

As shown in FIG. 3, the apparatus main unit 102 is provided on the front with a power switch SW1, a stop switch SW2, a first pressure display section 106, a second pressure display section 108, a first function stop switch SW3, and a second function stop switch SW4. The first pressure display section 106 and the second pressure display section 108 are panels for displaying the pressure values of the first balloon 60 and the second balloon 80 respectively. When an anomaly such as a balloon break occurs, an error code is displayed on the pressure display section 106, 108.

The first function stop switch SW3 and the second function stop switch SW4 are switches for turning on/off the function of an endoscope control channel A and the function of insertion aid instrument control channel B (described later) respectively. To use only either of the first balloon 60 and the second balloon 80, the function stop switch SW3 or SW4 of the unused balloon is operated for turning off the function. In the control channel A or B with the function turned off, air supply and suction completely stop and the pressure display section 106 or 108 of the channel is also turned off. Both the function stop switches SW3 and SW4 are turned off, whereby the initial state can be set, etc. For example, both the function stop switches SW3 and SW4 are turned off and all switches SW5 to SW9 of the hand switch 104 are pressed at the same time, whereby calibration for atmospheric pressure is exected.

The air supply-exhaust tube 110 for the first balloon 60 and the air supply-exhaust tube 120 for the second balloon 80 are connected to the front of the apparatus main unit 102. Backflow prevention units 112 and 122 for preventing backflow of a body fluid when the first balloon 60 is broken and when the second balloon 80 is broken are provided in the connection part between the tube 110 and the apparatus main unit 102 and that between the tube 120 and the apparatus main unit 102 respectively. Each of the backflow prevention units 112 and 122 is provided by building a filter for gas and liquid separation in a case shaped like a hollow disk (not shown) detachably attached to the apparatus main unit 102, and prevents liquid from flowing into the apparatus main unit 102 through the filter.

The pressure display sections 106 and 108, the function stop switches SW3 and SW4, and the backflow prevention units 112 and 122 are always placed as a constant layout of those for the endoscope 10 and those for the insertion aid instrument 70. That is, the pressure display section 106, the function stop switch SW3, and the backflow prevention unit 112 for the endoscope 10 are placed on the right relative to the pressure display section 108, the function stop switch SW4, and the backflow prevention unit 122 for the insertion aid instrument 70.

On the other hand, the hand switch 104 is provided with a stop switch SW5 like the stop switch SW2 of the apparatus main unit 102, an ON/OFF switch SW6 for giving a command of pressurization/decompression of the first balloon 60, a pause switch SW7 for holding the pressure of the first balloon 60, an ON/OFF switch SW8 for giving a command of pressurization/decompression of the second balloon 80, a pause switch SW9 for holding the pressure of the second balloon 80, a switch SW10 for setting the air supply flow rate and the exhaust flow rate for a small intestine, and a switch SW11 for setting the air supply flow rate and the exhaust flow rate for a large intestine. The hand switch 104 is electrically connected to the apparatus main unit 102 through a cord 130. A display section for indicating the air supply state or the exhaust state of each of the first balloon 60 and the second balloon 80 is provided on the hand switch 104 although it is not shown in FIG. 1.

Figure 4:
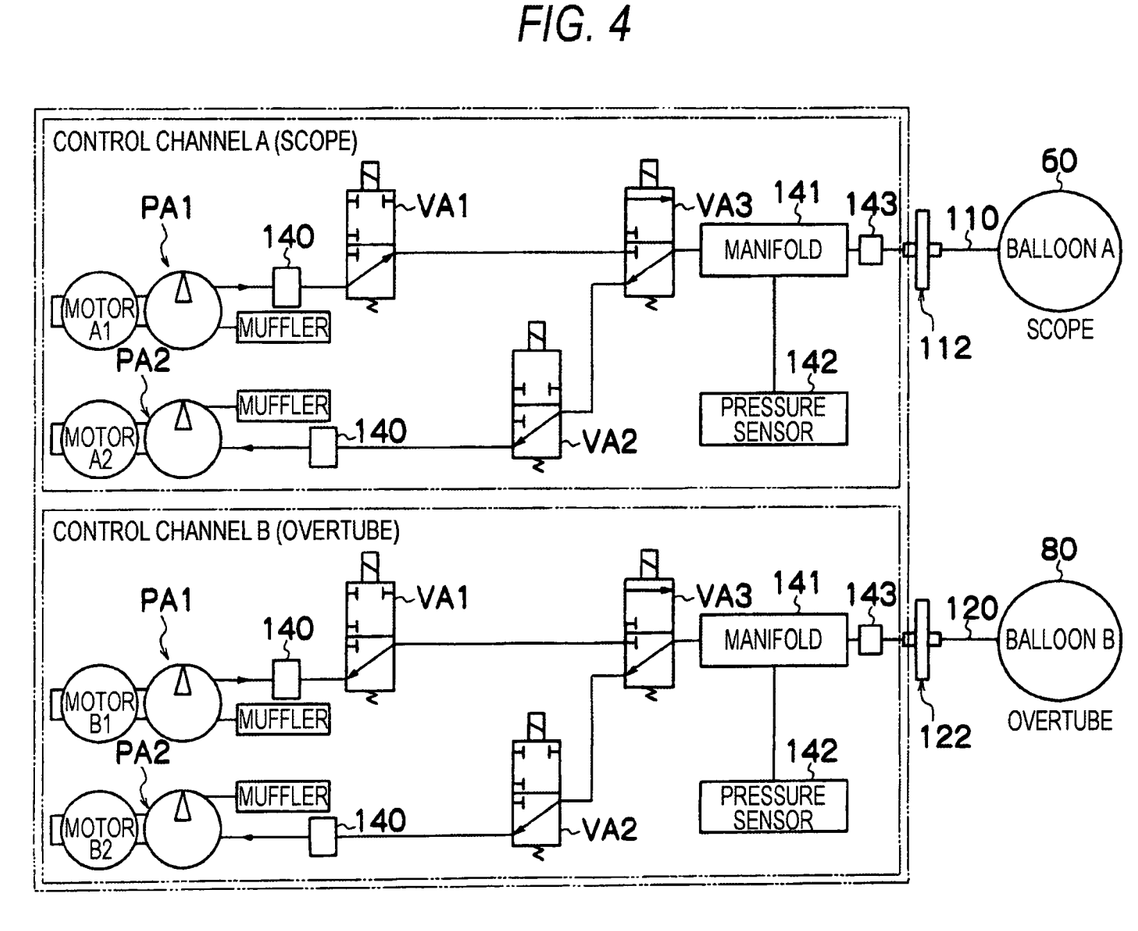
FIG. 4 is a circuit diagram to describe the internal configuration of the balloon control apparatus.

Next, the internal configuration of the balloon control apparatus 100 (apparatus main unit 102) will be described in detail with reference to FIG. 4. FIG. 4 is a circuit diagram to describe the internal configuration of the balloon control apparatus 100.

As shown in FIG. 4, the balloon control apparatus 100 mainly includes a control unit, such as a CPU, (not shown) for controlling the entire balloon control apparatus 100, and control channels A and B.

The control channel A is intended for controlling the first balloon 60 attached to the endoscope 10. It includes an electromagnetic valve VA3 for switching between air supply and exhaust, which are controlled by the control unit such as a CPU (not shown). If the electromagnetic valve VA3 is switched to the air supply position, an air supply line is established between the first balloon 60 and an air supply (pressurization) pump PA1. Therefore, if the air supply pump PA1 is operated, air is supplied to the first balloon 60 via the established air supply line. Accordingly, the first balloon 60 starts to expand.

On the other hand, if the electromagnetic valve VA3 is switched to the exhaust position, an exhaust line is established between the first balloon 60 and an exhaust (decompression) pump PA2. Therefore, if the exhaust pump PA2 is operated, air is exhausted from the first balloon 60 via the established supply line. Accordingly, the first balloon 60 starts to contract.

A flow rate controller 140 controlled by the control unit, such as a CPU, (not shown), is provided (on the piping) between the electromagnetic valve VA3 and the air supply pump PA1. For example, a needle flow rate control valve may be provided as the flow rate controller 140. The flow rate controller 140 can adjust the flow rate in the air supply line (air supply flow rate).

An electromagnetic valve VA1 for opening and closing controlled by the control unit, such as a CPU, (not shown), is provided (on the piping) between the electromagnetic valve VA3 and the air supply pump PA1. If the electromagnetic valve VA1 is closed, the air supply line to the first balloon 60 is brought to be a closed line. That is, if the electromagnetic valve VA1 is closed, the inside of the air supply line can be kept (eventually, the internal pressure of the first balloon 60) at a predetermined pressure.

Another flow rate controller 140 controlled by the control unit, such as a CPU, (not shown), is also provided (on the piping) between the electromagnetic valve VA3 and the exhaust pump PA2. This flow rate controller 140 can adjust the flow rate in the exhaust line (exhaust flow rate).

An electromagnetic valve VA2 for opening and closing controlled by the control unit, such as a CPU, (not shown), is provided (on the piping) between the electromagnetic valve VA3 and the exhaust pump PA2. If the electromagnetic valve VA2 is closed, the exhaust line from the first balloon 60 is brought to be a closed line. That is, if the electromagnetic valve VA2 is closed, the inside of the exhaust line (eventually, the internal pressure of the first balloon 60) can be kept at a predetermined pressure.

A pressure sensor 142 for detecting the pressure in a common line (eventually, the internal pressure of the first balloon 60) through a manifold 141 is provided (on the piping) between the electromagnetic valve VA3 and the backflow prevention unit 112. The pressure sensor 142 is connected to the control unit, such as a CPU, (not shown).

A flowmeter 143 (also called a "flow rate sensor") for detecting the flow rate (air supply flow rate, exhaust flow rate) in the common line is provided (on the piping) between the electromagnetic valve VA3 and the backflow prevention unit 112. The flowmeter 143 is connected to the control unit, such as a CPU, (not shown).

The control channel B is intended for controlling the second balloon 80 attached to the insertion aid instrument 70. The control channel B has the same configuration as the control channel A. Therefore, parts identical with those of the control channel A are denoted by the same reference numerals and will not be described again.

Next, the operation (pressurization process) of the described balloon control apparatus 100 will be described with reference to the accompanying drawings.

Figure 5:
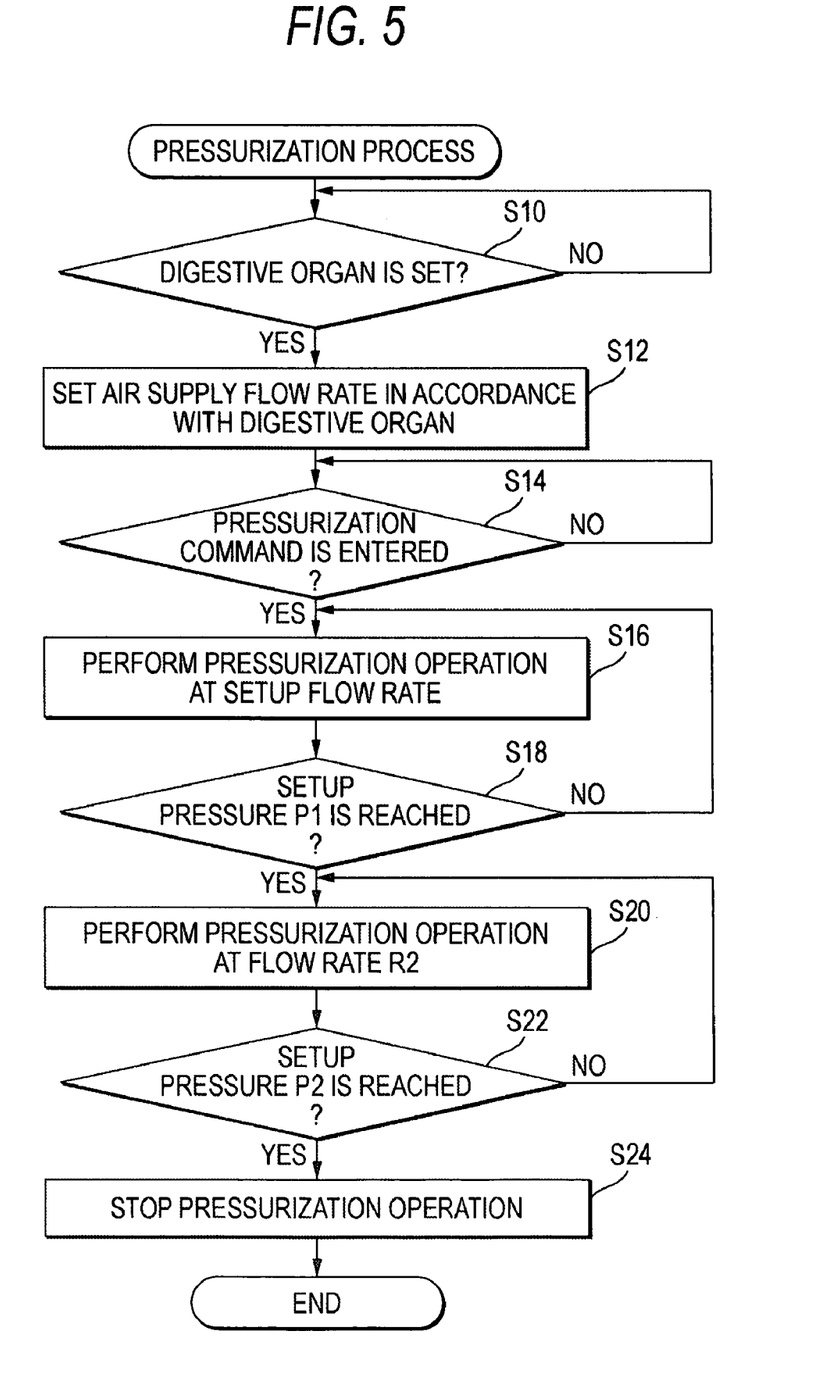
FIG. 5 is a flowchart to describe a pressurization process.

FIG. 5 is a flowchart to describe a pressurization process.

It is assumed that the following operation (the pressurization process) is implemented by turning on the power switch SW1 of the balloon control apparatus 100, reading a predetermined program into internal memory and is executing the read program by the control unit, such as a CPU, (not shown). The process for the control channel A will be described below.

The hand switch 104 of the balloon control apparatus 100 is provided with (i) the switch SW10 for setting the air supply flow rate for the small intestine and the exhaust flow rate for the small intestine, and (ii) the switch SW11 for setting the air supply flow rate for the large intestine and the exhaust flow rate for the large intestine (the switches SW10 and SW11 may serve as a part selection section). If the insert the endoscope 10 (insertion section 12) and the insertion aid instrument 70 are to be inserted into the small intestine, the operator operates the switch SW10. If the endoscope 10 (insertion section 12) and the insertion aid instrument 70 are to be inserted into the large intestine, the operator operates the switch SW11 (step S10).

If the switch SW10 is operated, an air supply flow rate SR1 for the small intestine and an exhaust flow rate HR1 for the small intestine are set (step S12). On the other hand, if the switch SW11 is operated, an air supply flow rate SR2 for the large intestine and an exhaust flow rate HR2 for the large intestine are set (the switches SW10 and SW11 may serve as a setting section).

Next, if the operator operates the switch SW6 and enters a pressurization command of the first balloon 60 (YES at step S14), the pressurization operation is started at the flow rate (SR1 or SR2) set at step S12 (step S16). That is, the electromagnetic valve VA3 is switched to the air supply position and the electromagnetic valve VA1 is opened, to thereby establish the air supply line between the first balloon 60 and the air supply (pressurization) pump PA1. In addition, the air supply (pressurization) pump PA1 is operated and further the flow rate controller 140 is controlled so that the air supply flow rate becomes the flow rate (SR1 or SR2) set at step S12.

Therefore, air is supplied to the first balloon 60 via the established supply line at the flow rate SR1 or SR2. Accordingly, the first balloon 60 starts to expand.

If the internal pressure of the first balloon 60 detected by the pressure sensor 142 reaches a previously setup pressure P1 (YES at step S18), the flow rate controller 140 is controlled so that the air supply flow rate becomes a predetermined flow rate R2 (smaller than the flow rate SR1 or SR2). Thus, the air supply flow rate is made large (flow rate SR1 or SR2) in the beginning and is lessened (flow rate R2) in the middle of the pressurization process. Thereby, it is made possible to increase the expansion speed of the first balloon 60.

Figure 6:
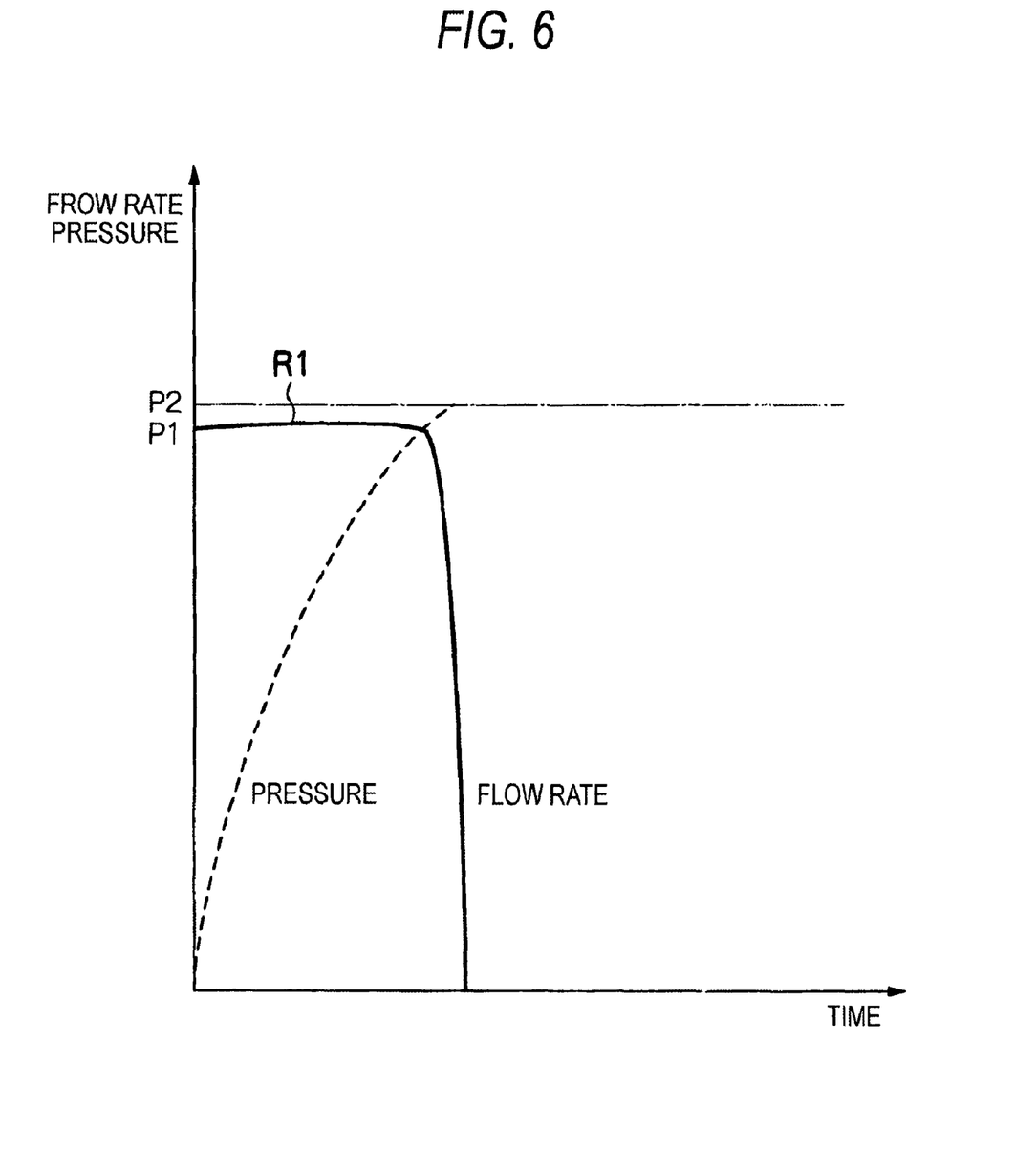
FIG. 6 is a graph to describe a flow rate adjustment pattern of a flow rate controller.

Next, when the internal pressure of the first balloon 60 detected by the pressure sensor 142 reaches a previously setup pressure P2 (larger than the setup pressure P1) (YES at step S22), the pressurization operation is stopped (step S24). That is, the electromagnetic valve VA1 is closed. Alternatively, the flow rate controller 140 is controlled so that the flow rate decreases with time, as shown in FIG. 6.

Accordingly, the closed line is established between the electromagnetic valve VA1 (or the flow rate controller 140) and the first balloon 60. That is, if the electromagnetic valve VA1 is closed, the inside of the air supply line (eventually, the internal pressure of the first balloon 60) can be kept at the predetermined pressure (the setup pressure P2).

As described above, according to the described pressurization process, the air supply flow rate is made large (flow rate R1) in the beginning and is lessened (flow rate R2) in the middle of the pressurization process (since the setup pressure P1 is reached). Thereby, it is made possible to increase the expansion speed of the first balloon 60.

The air supply flow rate SR1 or SR2 can be set by operating the switch SW10 or SW11 in accordance with the digestive tract into which the endoscope insertion section 12 is to be inserted. That is, the air supply flow rate can be set in accordance with the type of digestive tract in such a manner that if the digestive tract is the small intestine, the flow rate SR1 is set, and if the digestive tract is the large intestine, the flow rate SR2 (=SR1×3) is set. Formerly, the time required until the first balloon 60 expands and contacts the intestinal wall and the setup pressure P2 is reached was about 10 seconds for the small intestine and about 30 seconds for the large intestine. To the contrary, since the flow rates are set as described above, the time until the internal pressure of the first balloon 60 reaches the setup pressure P2 (namely, the time until the first balloon 60 is fixed) in the large intestine becomes about one third and becomes roughly equal to the required time in the small intestine. That is, it is made possible to eliminate (or lessen) the difference in time until the internal pressure of the first balloon 60 reaches the setup pressure P2 (namely, the time until the first balloon 60 is fixed) regardless of the type of digestive tract.

The pressurization process for the second balloon 80 is also executed in the control channel B. This process is similar to the pressurization process for the control channel A described above and therefore will not be described again.

Next, the operation (decompression process) of the balloon control apparatus 100 will be described with reference to the accompanying drawings.

Figure 7:
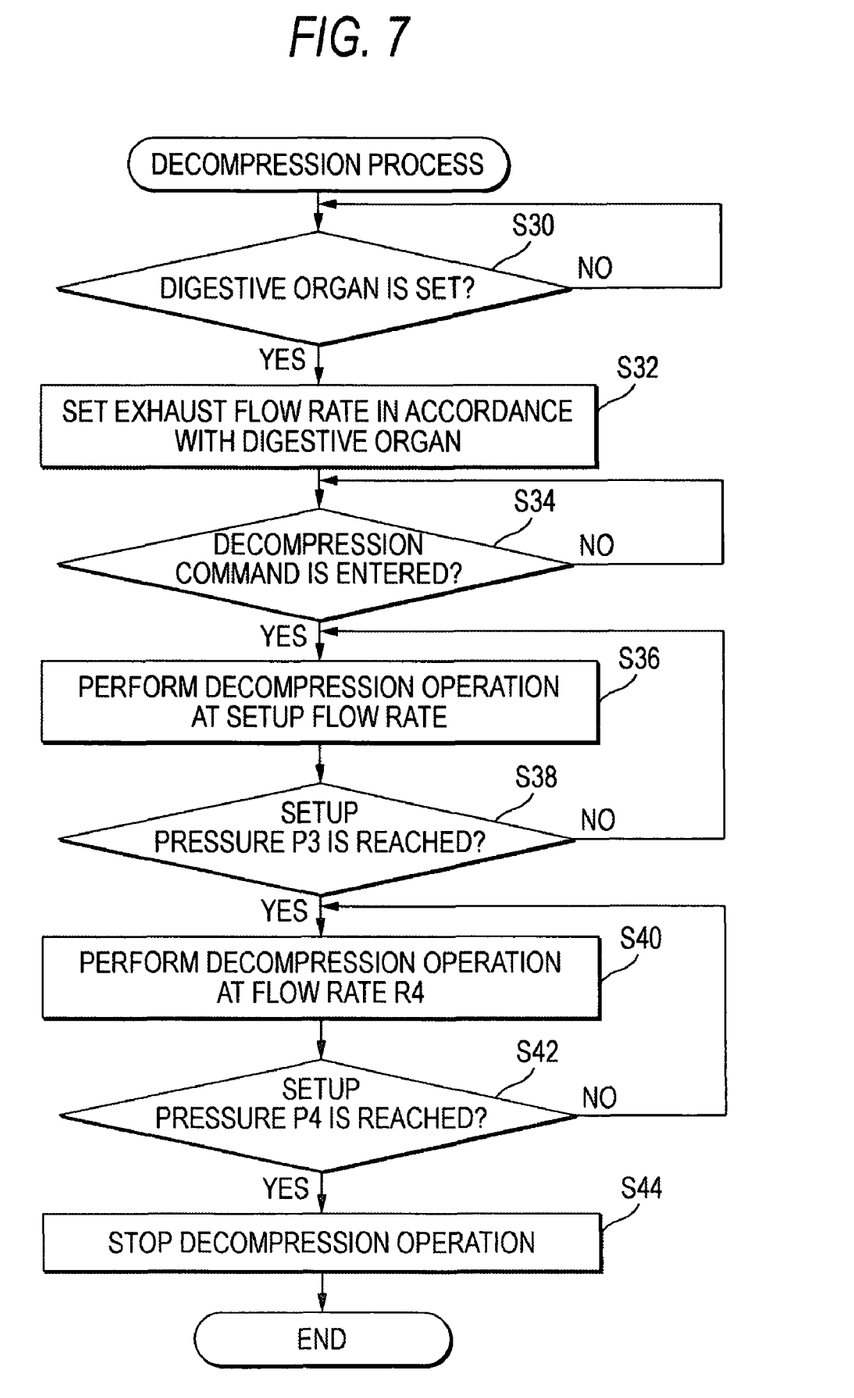
FIG. 7 is a flowchart to describe a decompression process.

FIG. 7 is a flowchart to describe a decompression process.

It is assumed that the following operation (decompression process) is implemented by turning on the power switch SW1 of the balloon control apparatus 100, reading a predetermined program into the internal memory and executing the read program by the control unit, such as a CPU, (not shown). The process for the control channel A will be described below.

The hand switch 104 of the balloon control apparatus 100 is provided with (i) the switch SW10 for setting the air supply flow rate for the small intestine and the exhaust flow rate for the small intestine and (ii) the switch SW11 for setting the air supply flow rate for the large intestine and the exhaust flow rate for the large intestine. To insert the endoscope 10 (insertion section 12) and the insertion aid instrument 70 into the small intestine, the operator operates the switch SW10. To insert the endoscope 10 (insertion section 12) and the insertion aid instrument 70 into the large intestine, the operator operates the switch SW11 (step S30).

If the switch SW10 is operated, the air supply flow rate SR1 for the small intestine and the exhaust flow rate HR1 for the small intestine are set (step S32). On the other hand, if the switch SW11 is operated, the air supply flow rate SR2 for the large intestine and the exhaust flow rate HR2 for the large intestine are set.

Next, if the operator operates the switch SW6 and enters a decompression command of the first balloon 60 (YES at step S34), the decompression operation is started at the flow rate (HR1 or HR2) set at step S32 (step S36). That is, the electromagnetic valve VA3 is switched to the exhaust position, the electromagnetic valve VA1 is closed and the electromagnetic valve VA2 is opened. Thereby, an exhaust line is established between the first balloon 60 and the exhaust (decompression) pump PA2. In addition, the exhaust (decompression) pump PA2 is operated and further the flow rate controller 140 is controlled so that the exhaust flow rate becomes the flow rate (HR1 or HR2) set at step S32.

As a result, air is exhausted from the first balloon 60 via the setup exhaust line at the flow rate HR1 or HR2. Accordingly, the first balloon 60 starts to contract.

If the internal pressure of the first balloon 60 detected by the pressure sensor 142 reaches a previously setup pressure P3 (YES at step S38), the flow rate controller 140 is controlled so that the exhaust flow rate becomes a predetermined flow rate R4 (smaller than the flow rate HR1 or HR2). Thus, the exhaust flow rate is made large (flow rate HR1 or HR2) in the beginning and is lessened (flow rate R4) in the middle of the decompression process. Thereby, it is made possible to increase the contracting speed of the first balloon 60.

Figure 8:
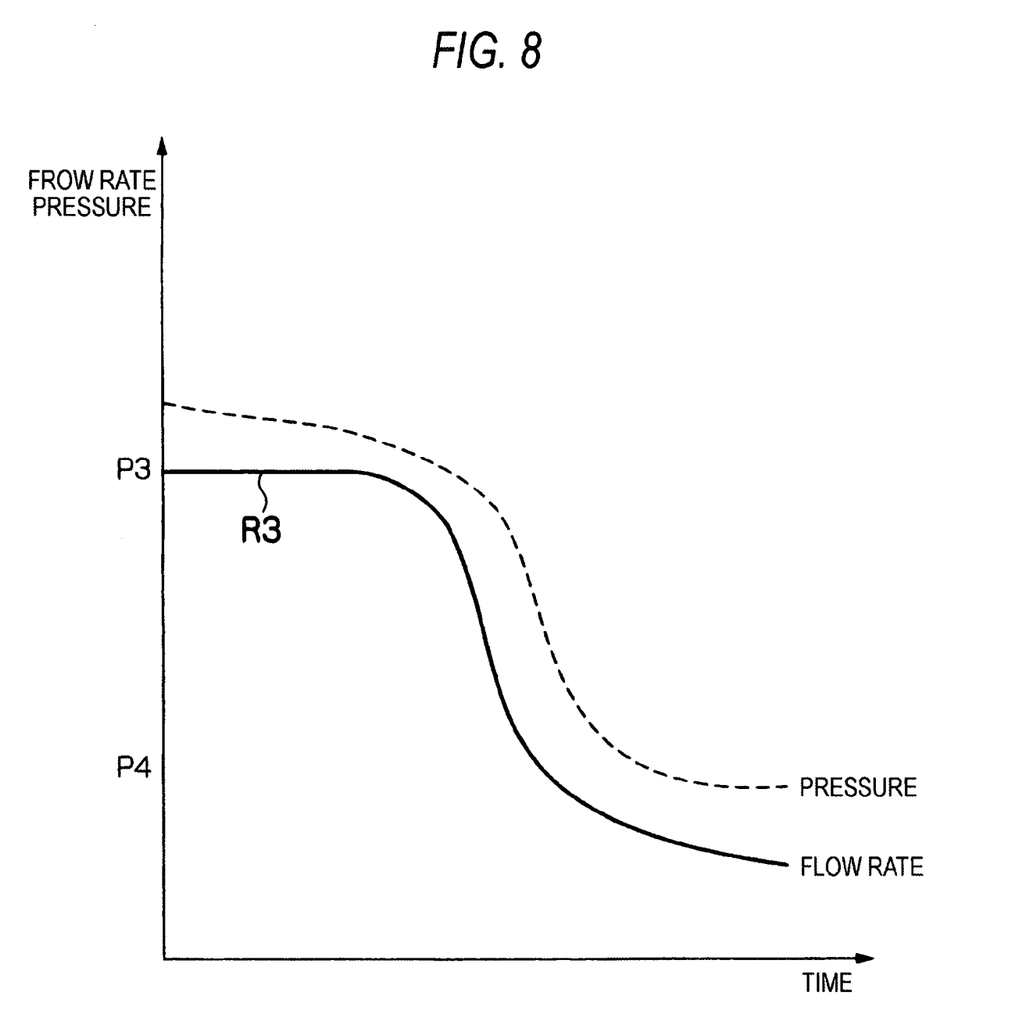
FIG. 8 is a graph to describe a flow rate adjustment pattern of a flow rate controller.

Next, when the internal pressure of the first balloon 60 detected by the pressure sensor 142 reaches a previously setup pressure P4 (smaller than the setup pressure P3) (YES at step S42), the decompression operation is stopped (step S44). That is, the electromagnetic valve VA2 is closed. Alternatively, the flow rate controller 140 is controlled so that the flow rate decreases with time, as shown in FIG. 8.

Accordingly, a closed line is established between the electromagnetic valve VA2 (or the flow rate controller 140) and the first balloon 60. That is, if the electromagnetic valve VA2 is closed, the inside of the exhaust line (eventually, the internal pressure of the first balloon 60) can be kept at the predetermined pressure (setup pressure P4).

As described above, according to the described decompression process, the exhaust flow rate is made large (flow rate HR1, HR2) in the beginning and is lessened (flow rate R4) in the middle of the decompression process (since the setup pressure P3 is reached). Thereby, it is made possible to increase the contracting speed of the first balloon 60.

The exhaust flow rate HR1 or HR2 can be set by operating the switch SW10 or SW11 in accordance with the digestive tract into which the endoscope insertion section 12 is to be inserted. That is, the exhaust flow rate can be set in accordance with the type of digestive tract in such a manner that if the digestive tract is a small intestine, the flow rate HR1 is set and that if the digestive tract is a large intestine, the flow rate HR2 (=HR1×3) is set. Formerly, the time required until the first balloon 60 contracts and the setup pressure P4 is reached was about 10 seconds for the small intestine and about 30 seconds for the large intestine. To the contrary, since the flow rates are set as described above, the time until the internal pressure of the first balloon 60 reaches the setup pressure P4 in the large intestine becomes about one third and becomes roughly equal to the required time in the small intestine. That is, it is made possible to eliminate (or lessen) the difference in time until the internal pressure of the first balloon 60 reaches the setup pressure P4 regardless of the type of digestive tract.

A decompression process of the second balloon 80 is also executed in the control channel B. This decompression process is similar to the decompression process in the control channel A described above and therefore will not be discussed again.

Next, a modified example will be described.

Figure 9:
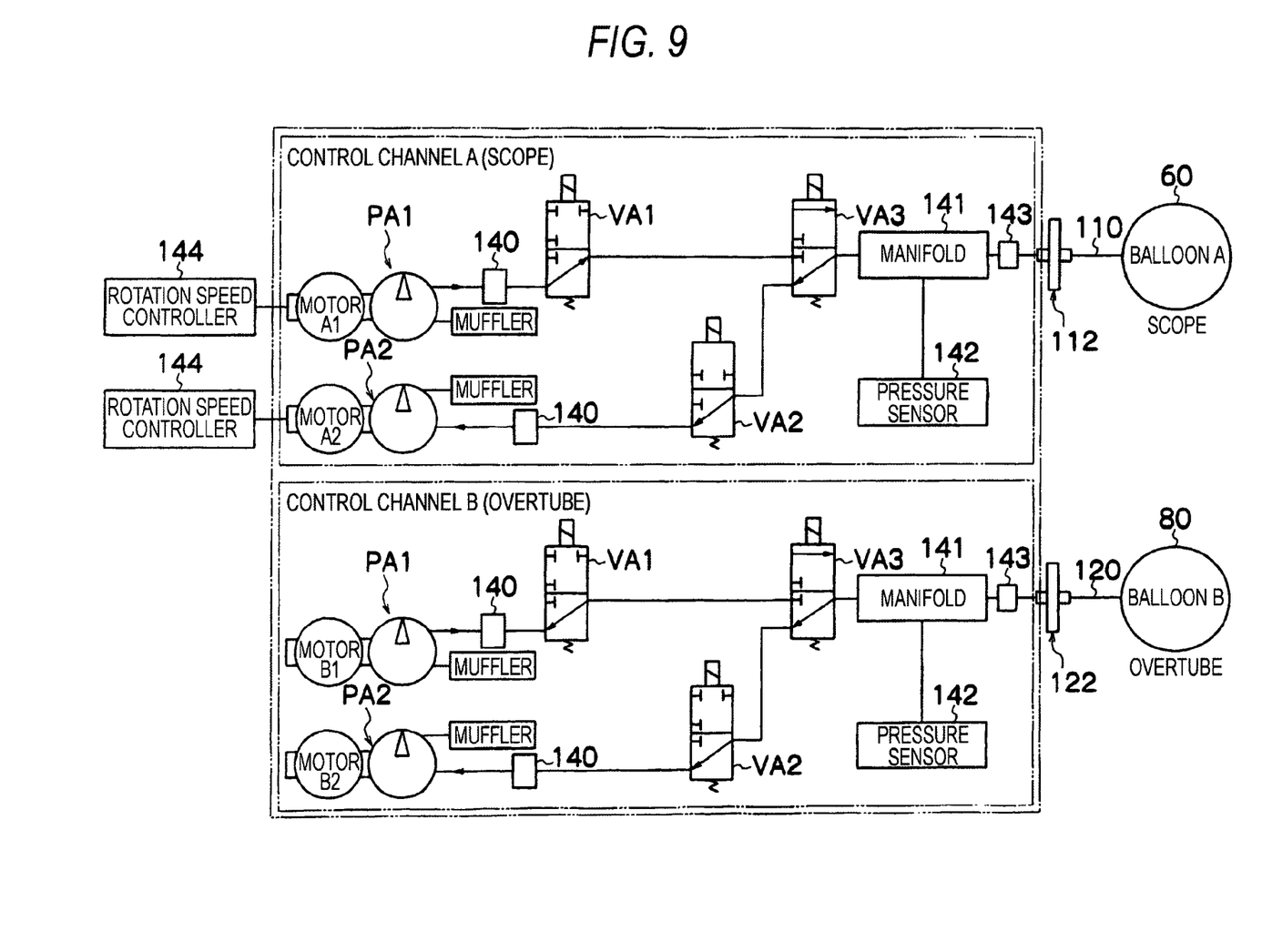
FIG. 9 is a circuit diagram to describe the internal configuration of a modified example of a balloon control apparatus.

In the embodiment described above, the air supply flow rate and the exhaust flow rate are controlled using the needle flow rate control valve controlled by the control unit such as a CPU. However, the invention is not limited thereto e. For example, as shown in FIG. 9, rotation speed controllers 144 controlled by the control unit such as a CPU (not shown) may control a motor for driving the air supply pump PA1 and a motor for driving the exhaust pump PA2, to thereby control the air supply flow rate and the exhaust flow rate. Alternatively, a manifold containing plural fixed throttles may be used and the throttles may be switched from one to another by a control unit, such as a CPU, for controlling the air supply flow rate and the exhaust flow rate.

In the embodiment described above, the operator selects the type of digestive tract (small intestine or large intestine) by operating the switch SW10 or SW11, the flow rate is set in accordance with the selected digestive tract, and air is supplied or is exhausted at the setup flow rate. However, the invention is not limited thereto. For example, any other digestive tract than the small intestine or large intestine may be able to be selected (for example, by providing an additional selection switch). Alternatively, since it is considered that the digestive tract diameter varies depending on the gender or the age, the operator may be allowed to specify (or select) an attribute of subject, such as the gender and the age together with the type of digestive tract (this configuration may correspond to an attribute specification section) and the flow rate may be set in accordance with the specified attributes such as the digestive tract, the gender and the age and air may be supplied or be exhausted at the setup flow rate.

Alternatively, the following configuration may be adopted. The endoscope 10 is connected to the connection part on the front of the processor 26, the processor 26 determines the use of the endoscope 10 connected to the connection part (the processor 26 may serve as a use determination section) and transmits the determined use of the endoscope 10 via a cable (not shown) for connecting the processor 26 and the balloon control apparatus 100 to the balloon control apparatus 100. The balloon control apparatus 100 then sets the flow rate in accordance with the determined use of the endoscope 10 and supplies or exhausts air at the setup flow rate, as shown in FIG. 1.

Various means may be adopted as the use determination section for determining the use of the endoscope. For example, the following configuration may be adopted. Identifiers of endoscopes (for example, large intestine endoscope ID if the endoscope is a large intestine endoscope; small intestine endoscope ID if the endoscope is a small intestine endoscope) are stored in the endoscope 10 (e.g. its internal memory). When an endoscope 10 is connected to the connection part on the front of the processor 26, the processor 26 reads the identifier from the endoscope 10 connected to the connection part (the processor 26 may serve as a reading section), and determines the use of the endoscope 10 connected to the connection part on the front of the processor 26 based on the read identifier (for example, by referencing a table where the identifiers and the uses are associated with each other).

According to this configuration, when the endoscope 10 is connected to the processor 26, the identifier can be read from the endoscope 10 (for example, endoscope ID), the use of the endoscope 10 (for example, large intestine endoscope or small intestine endoscope) can be automatically recognized based on the read identifier, and the air supply flow rate and/or the exhaust flow rate is set in accordance with the recognized use of the endoscope 10.

To apply a single balloon method of using a balloon of the endoscope 10 only and pulling in an intestinal tract, it is also considered that a larger flow rate is set than that when the usual double balloon method is applied. That is, to pull in an intestinal tract according to the single balloon method, the operation sequence of inflating a balloon and fixing the intestinal tract and pulling in the intestinal tract in the state and then advancing the endoscope before the balloon is contracted and the pulled-in intestinal tract is restored to the former state and again inflating the balloon and fixing the intestinal tract and pulling in the intestinal tract in the state is repeated. Thus, the balloon must be inflated at the next location before the intestinal tract is restored to the former state, and it is necessary to inflate and contract the balloon in an instant. Then, the switch SW11 (corresponding to procedure selection section of the invention) is operated. Alternatively, a high-speed switch corresponding to the switch SW11 is provided additionally and is operated. In so doing, it is made possible to set the flow rate in response to the procedure in such a manner that if the operator selects the single balloon method by operating the switch SW11, the flow rate R1 is set and that if the operator selects the double balloon method by operating the switch SW10 or a low-speed switch corresponding to the switch SW10, the flow rate R2 (R1>R2) is set. Therefore, the single balloon method is selected and the flow rate is set large, whereby the expansion and contraction time of the first balloon 60 is shortened and return of the pulled-in intestinal tract can be lessened, so that the single balloon method would also make it possible to conduct intestinal inspection efficiently.

To switch to the air supply flow rate and/or the exhaust flow rate between the single balloon method and the double balloon method, instead of using the switch, the identifier of the endoscope may be read by the processor, the single balloon method or the double balloon method may be determined based on the read identifier, and automatic switching to the appropriate air supply flow rate and/or exhaust flow rate may be performed.

While the preferred embodiment of the invention has been described, such description is for illustrative purposes only in every respect. The invention is not limited by the description. Various changes and modifications can be made in the invention without departing from the spirit and scope thereof.

What is claimed is:

1. A balloon control apparatus comprising:
   a balloon attached to an insertion section of an endoscope and/or an insertion aid instrument for guiding insertion of the insertion section of the endoscope;
   a flow rate adjustment section that adjusts an air supply flow rate to the balloon and/or an exhaust flow rate from the balloon;
   a setting section that sets the air supply flow rate and/or the exhaust flow rate;
   a control section that controls the flow rate adjustment section so that the air supply flow rate to the balloon and/or the exhaust flow rate from the balloon become the air supply flow rate and/or the exhaust flow rate set by the setting section; and
   a part selection section that allows an operator to select an intracoelomic part into which the insertion section of the endoscope and/or the insertion aid instrument is to be inserted, wherein:
   the setting section sets the air supply flow rate or the exhaust flow rate in accordance with the intracoelomic part selected by the part selection section,
   the control section controls an internal pressure of the balloon so as to be a predetermined pressure by controlling the flow rate adjustment section, and
   a time until the internal pressure of the balloon reaches the predetermined pressure in case that the intracoelomic part has a large diameter is approximately equal to a time until the internal pressure of the balloon reaches the predetermined pressure in case that the intracoelomic part has a small diameter.

2. The apparatus according to claim 1, further comprising a procedure selection section that allows an operator to select a procedure of the endoscope, wherein:
   the setting section sets the air supply flow rate or the exhaust flow rate in accordance with the procedure selected by the procedure selection section.

3. The apparatus according to claim 1, further comprising:
   an attribute specification section that allows an operator to specify an attribute of a subject into whom the insertion section of the endoscope and/or the insertion aid instrument is to be inserted, wherein:
   the setting section sets the air supply flow rate or the exhaust flow rate in accordance with to the intracoelomic part selected by the part selection section and the attribute of the subject specified by the attribute specification section.

4. The apparatus according to claim 1, wherein the intracoelomic part into which the insertion section of the endoscope and/or the insertion aid instrument is to be inserted is a digestive tract.

5. The apparatus according to claim 1, wherein the control section makes the air supply flow rate and/or the exhaust flow rate larger in the beginning of the air supply and/or the exhaust, and makes the air supply flow rate and/or the exhaust flow rate less in the middle of the air supply and/or the exhaust.

6. An endoscope system comprising:
   a balloon attached to an insertion section of an endoscope and/or an insertion aid instrument for guiding insertion of the insertion section of the endoscope;
   a flow rate adjustment section that adjusts an air supply flow rate to the balloon and/or an exhaust flow rate from the balloon;
   a setting section that sets an air supply flow rate and/or an exhaust flow rate;
   a control section that controls the flow rate adjustment section so that the air supply flow rate to the balloon and/or the exhaust flow rate from the balloon become the air supply flow rate and/or the exhaust flow rate set by the setting section;
   a connection part to which the endoscope is connected; and
   a use determination section that determines a use of the endoscope connected to the connection part, wherein:
   the setting section sets the air supply flow rate or the exhaust flow rate in accordance with the use of the endoscope determined by the use determination section,
   the control section controls an internal pressure of the balloon so as to be a predetermined pressure by controlling the flow rate adjustment section, and
   a time until the internal pressure of the balloon reaches the predetermined pressure in case that the intracoelomic part has a large diameter is approximately equal to a time until the internal pressure of the balloon reaches the predetermined pressure in case that the intracoelomic part has a small diameter.

7. The system according to claim 6, wherein the use determination section includes a reading section that reads an identifier from the endoscope connected to the connection part and determines the use of the endoscope connected to the connection part based on the identifier read by the reading section.

8. The apparatus according to claim 6, wherein the control section makes the air supply flow rate and/or the exhaust flow rate larger in the beginning of the air supply and/or the exhaust, and makes the air supply flow rate and/or the exhaust flow rate less in the middle of the air supply and/or the exhaust.

* * * * *